United States Patent [19]

Ogoshi et al.

[11] 3,997,575

[45] Dec. 14, 1976

[54] BLEACHING METHOD FOR SULFONIC ACID

[75] Inventors: Toshiaki Ogoshi, Funabashi; Yukio Kusumi, Chiba, both of Japan

[73] Assignee: Lion Fat & Oil Co., Ltd., Tokyo, Japan

[22] Filed: Nov. 4, 1974

[21] Appl. No.: 520,436

[30] Foreign Application Priority Data

Nov. 12, 1973 Japan ............................ 48-126235

[52] U.S. Cl. ........................... 260/400; 260/481 R; 260/505 S; 260/513 R; 260/513 T
[51] Int. Cl.$^2$ ........................................ C07C 139/14
[58] Field of Search ............ 260/400, 481 R, 513 R, 260/513 T, 505 S

[56] References Cited

UNITED STATES PATENTS

| | | | |
|---|---|---|---|
| 2,806,055 | 9/1957 | Feighner | 260/505 S |
| 3,159,657 | 12/1964 | Wulff et al. | 260/400 |

Primary Examiner—Patrick P. Garvin
Attorney, Agent, or Firm—Woodhams, Blanchard and Flynn

[57] ABSTRACT

A bleaching method for sulfonic acid, which comprises the process of bleaching sulfonic acid by adding (1) 0.5 – 20 parts by weight of primary or secondary aliphatic alcohol having 1 – 12 carbon atoms, (2) 0.5 – 10 parts by weight of a bleaching agent consisting of peroxide and (3) 0.1 – 10 parts by weight of water relative to 100 parts by weight of sulfonic acid.

8 Claims, No Drawings

BLEACHING METHOD FOR SULFONIC ACID

BACKGROUND OF THE INVENTION

1. Field of the Invention

The present invention relates to a method of bleaching sulfonic acid by the use of a bleaching agent consisting of peroxide and water in the presence of aliphatic alcohol having 1–12 carbon atoms and under acid condition.

2. Description of the Prior Art

There are known varieties of methods for bleaching sulfonic acid under acid condition. For instance, British Pat. No. 983,056 discloses a method of bleaching with hydrogen peroxide, sodium hypochlorite or the like before or after hydrolyzing α-olefin sulfonate, and Japanese Patent Publication No. 956/1966 discloses a bleaching method comprising the process of bleaching a highly colored sulfonic acid with hydrogen peroxide, neutralizing thereafter and bleaching again with hypochlorous acid or the like.

According to these known methods of bleaching, however, a satisfactory result cannot be expected in the case of sulfonic acids that are highly colored and hard to bleach, because a large quantity of bleaching agent is added, the effect obtained by adding a large quantity of bleaching agent is not sufficient, and a deterioration of the color takes place with the passage of time.

SUMMARY OF THE INVENTION

The object of the present invention is to provide a method of bleaching sulfonic acid, which method gives higher bleaching efficiency and can produce a sulfonic acid having a stable color free from deterioration with the passage of time. The bleaching method according to the present invention is characterized by the process of bleaching sulfonic acid by adding 0.5 –20 parts by weight of primary or secondary aliphatic alcohol having 1–12 carbon atoms, 0.5–10 parts by weight of a bleaching agent consisting of peroxide and 0.1–10 parts by weight of water relative to 100 parts by weight of sulfonic acid.

DETAILED DESCRIPTION OF THE INVENTION

The sulfonic acid herein means sulfofatty acid ester having 6–20 carbon atoms, sulfofatty acid having 6–20 carbon atoms, alkylbenzene sulfonic acid having a side chain of 12–14 carbon atoms, α-olefin sulfonic acid having 12–20 carbon atoms. etc., and particularly sulfofatty acid ester having 6–20 carbon atoms and sulfofatty acid having 6–20 carbon atoms are suitable for use in the present invention, while sulfuric acid ester is unsuitable for use in the present invention.

It is possible to perform the bleaching of these sulfonic acids by effecting reaction under prescribed conditions upon adding a small quantity of water to said sulfonic acids and further adding thereto aliphatic alcohol and peroxide.

As the aliphatic alcohol for this purpose, primary or secondary alcohols having 1–12 carbon atoms are preferable, and to cite instances, there are methyl alcohol, ethyl alcohol, propyl alcohol, hexyl alcohol, octyl alcohol, lauryl alcohol, isopropyl alcohol, ethylene glycol, glycerin, trimethylol propane, etc. The applicable amount of these aliphatic alcohols is in the range of 0.5–20% by weight, preferably 1–15% by weight, relative to sulfonic acid: in the case where the applied amount is less than 0.5% by weight, the effect of addition of said alcohols cannot be displayed sufficiently in bleaching, while in the case where the applied amount is excessive, it causes a lowering of the purity of the sulfonic acid and therefore application of less than 20% by weight is appropriate. The bleaching agent consisting of peroxide for use in the present invention includes hydrogen peroxide, sodium perborate, sodium percarbonate, etc., and the applicable amount thereof is in the range of 0.5–10% by weight, preferably 1–5% by weight, relative to sulfonic acid: in the case where the applied amount is less than 0.5% by weight, the effect of addition of said bleaching agent cannot be displayed sufficiently in bleaching, while even in the case where the applied amount is in excess of 10% by weight, any furtherance of bleaching effect cannot be expected and such overuse is wasteful.

The amount of water to be added to sulfonic acid is in the range of 0.1–10% by weight, preferably 1–4% by weight relative to sulfonic acid. The use of water is for the purpose of hydrating the free sulfuric anhydride contained in sulfonic acid, but application of too much water will enhance the viscosity of the sulfonic acid to make it difficult to stir. Therefore, the amount of water to be added to sulfonic acid must be confined to the minimum as required.

In the present invention, the foregoing aliphatic alcohol, bleaching agent consisting of peroxide and water are added to sulfonic acid in appropriate amounts respectively, and reaction is effected at a fixed temperature for bleaching for a fixed period of time for bleaching. This temperature for bleaching is in the range of 40° – 90° C: application of a temperature lower than 40° C is unsuitable as it entails requirement for many hours in bleaching, while application of an excessively high temperature for bleaching causes reversion of the color after the bleaching treatment, resulting in deterioration of the color. Therefore, the appropriate temperature for bleaching in the present invention, though it depends upon the kind of sulfonic acid, is in the range of 40° –90° C. When the method of the present invention is put into practice at a temperature in this range, the bleaching can be completed in 15–120 minutes. Subsequent to said bleaching, the sulfonic acid may be neutralized as occasion demands.

As described in the foregoing, the present invention renders it possible to realize a sufficient bleaching effect by the use of a small amount of peroxide and to produce a stable sulfonic acid whose color is free from deterioration with the passage of time. Especially in respect of sulfofatty acid ester, the partial scission of the ester linkage is apt occur on the occasion of sulfonation, addition of water or bleaching, and thereby the sulfofatty acid ester was partly converted into sulfofatty acid. But, according to the method of the present invention, sulfofatty acid is esterified again simultaneously with the bleaching so that the formation of sulfofatty acid having low efficiency as the surface active agent can be substantially zero.

The reason why such an excellent effect can be displayed in the process of bleaching is not yet clarified, but in view of the fact that application of n-hexane or carbon tetrachloride cannot bring about such an effect, it may safely be said that this effect is not attributable to the decrease of viscosity.

PREFERRED EMBODIMENTS OF THE INVENTION

In the following embodiments of the present invention, the measurements of the change of color and viscosity were conducted under the following conditions:

Conditions for measurement of color:
  sample: 5% aqueous solution of sulfonate
  measurement: by absorptiometric method (by the use of Spectrophotometer Model-139, HITACHI SEISAKUSHO K.K.)
  wave-length : 420 m$\mu$
  width of slit: 0.05 mm
  indication of value: degree of light-absorption by actual measurement $(-\log T) \times 10^3$ Condition for measurement of viscosity:
  visco-meter: Model BL type (Tokyo Keiki K.K.)
  temperature: at 80° C

EXAMPLE 1

After putting 290g of a hard hydrogenated beef-tallow fatty acid methyl ester in a 600 ml vessel, SO$_3$ gas having concentration of 5% diluted with nitrogen gas was blown into said methyl ester material while heating it up to 50° C and then raising the temperature gradually, and the sulfonation reaction was concluded after making the molar ratio of SO$_3$ to said methyl ester to be 1.3:1 at 80° C. After aging the resulting sulfonate at 80° C for 15 minutes, by adding 1% of water thereto, the corresponding sulfonic acid was prepared. Subsequently, after putting 100g of this sulfonic acid in a 300 ml conical flask equiped with a condenser, 7.7g of methyl alcohol and 4.0g of 30% hydrogen peroxide solution were added thereto with stirring, whereby bleaching was effected at 80° C for 30 minutes. The viscosity of mixture in the early stage of bleaching being 21 centipoise. The thus bleached sulfonic acid was neutralized with 4% aqueous solution of NaOH, and a part of the sulfonate was adjusted to be a 5% aqueous solution and the color thereof was measured and it was 86. Further, no sulfofatty acid was detected in the bleached product. In this connection, when the color of a 5% aqueous solution of sodium sulfonate as neutralized without bleaching was measured, the value was 2400. On the other hand, in the case where the bleaching was effected without applying methyl alcohol and the color of a 5% aqueous solution of the product obtained by neutralizing the thus bleached sulfonic acid was measured, the value was 800. Further, the concentration of sodium sulfofatty acid was 18% by weight in sodium sulfonate. The viscosity of the mixture in the early stage of bleaching was 210 centipoise.

EXAMPLE 2

After sulfonating a hard hydrogenated beef-tallow fatty acid methyl ester in the same way as in Example 1, 100g of the resulting sulfonic acid was placed in a 300 ml conical flask equipped with a condenser, 11.1g of ethyl alcohol together with 4.0g of 30% hydrogen peroxide solution were added thereto with stirring, and bleaching was effected at 80° C for 30 minutes. The viscosity of the mixture in the early stage of bleaching was 35 centipoise. The thus bleached sulfonic acid was neutralized with 4% aqueous solution of NaOH, and a part of the sulfonate was adjusted to be a 5% aqueous solution and the color thereof was measured and it was 106. Further no sulfofatty acid was detected in the bleached product.

EXAMPLE 3

After sulfonating a hard hydrogenated beef-tallow fatty acid methyl ester in the same way as in Example 1, 100g of the resulting sulfonic acid was placed in a 300 ml conical flask equipped with a condenser, then 10g of lauryl alcohol and 4.0g of 30% hydrogen peroxide solution were added thereto with stirring, and bleaching was effected at 80° C for 30 minutes. The viscosity of the mixture in the early stage of bleaching was 125 centipoise. The thus bleached sulfonic acid was neutralized with 4% aqueous solution of NaOH, and then a part of the sulfonate was adjusted to be a 5% aqueous solution and the color thereof was measured and it was 186. Further no sulfofatty acid was detected in the bleached product.

EXAMPLE 4

After sulfonating a hard hydrogenated beef-tallow fatty acid methyl ester in the same way as in Example 1, 100g of the resulting sulfonic acid was placed in a 300 ml conical flask equipped with a condenser, then 10g of ethylene glycol and 4.0g of 30% hydrogen peroxide solution were added thereto with stirring, and bleaching was effected at 80° C for 30 minutes. The viscosity of the mixture in the early stage of bleaching was 81 centipoise. The thus bleached sulfonic acid was neutralized with 4% aqueous solution of NaOH, and then a part of the sulfonate was adjusted to be a 5% aqueous solution and the color thereof was measured and it was 124. Further no sulfofatty acid was detected in the bleached product.

COMPARATIVE EXAMPLE 1

After sulfonating a hard hydrogenated beef-tallow fatty acid methyl ester in the same way as in Example 1, 100g of the resulting sulfonic acid was placed in a 300 ml conical flask equipped with a condenser, then 15g of n-hexane and 4.0g of 30% hydrogen peroxide solution were added thereto with stirring, and bleaching was effected at 80° C for 30 minutes. The viscosity of the mixture in the early stage of bleaching was 20 centipoised. The thus bleached sulfonic acid was neutralized with 4% aqueous solution of NaOH, and then a part of the sulfonate was adjusted to be a 5% aqueous solution and the color thereof was measured and it was 510. However the concentration of sodium sulfofatty acid was 18% by weight in sodium sulfonate.

COMPARATIVE EXAMPLE 2

After sulfonating a hard hydrogenated beef-tallow fatty acid methyl ester in the same way as in Example 1, 100 g of the resulting sulfonic acid was placed in the same vessel as that in Comparative Example 1, then 18g of carbon tetrachloride and 4.0g of 30% hydrogen peroxide solution was added thereto with stirring, and bleaching was effected at 80° C for 30 minutes. The viscosity of the mixture in the early stage of bleaching was 18 centipoise. The thus bleached sulfonic acid was neutralized in the same way as in Comparative Example 1, then, a part of sulfonate was adjusted to be a 5% aqueous solution and the color thereof was measured and it was 600. Further, the concentration of sodium sulfofatty acid was 20% by weight in sodium sulfonate.

EXAMPLE 5

After putting 240g of straight-chain dodecyl benzene in a 600 ml vessel, SO$_3$ gas having concentration of 8% as diluted with nitrogen gas was blown into said alkyl benzene material while heating it up to 50° C so as to make the molar ratio of SO₃ to said alkyl benzene 1.10:1, to effect sulfonation. After aging the resulting sulfonate at 50° C for 30 minutes, 30g of water were added thereto. Subsequently, after putting 100g of the thus obtained sulfonic acid in a 300 ml conical flask equipped with a condenser, 7.7g of methyl alcohol and 1g of 30% hydrogen peroxide solution were added thereto with stirring, whereby bleaching was effected at 80° C for 30 minutes. The viscosity of mixture in the early stage of bleaching was 50 centipoise. The thus bleached sulfonic acid was neutralized with 4% aqueous solution of NaOH, and then a part of sulfonate was adjusted to be a 5% aqueous solution and the color thereof was measured and it was 6.

In this connection, when the color of a 5% aqueous solution of sodium sulfonate as neutralized without bleaching was measured, the value was 46.

Further, in the case where the bleaching was effected at 80° C for 30 minutes by adding 1g of 30% hydrogen peroxide solution without applying methyl alcohol and the thus bleached sulfonic acid was neutralized with 4% aqueous solution of NaOH, then, a part of sulfonate was adjusted to be a 5% aqueous solution and the color thereof was measured, the value was 14. The the viscosity of mixture in the early stage of the bleaching was 600 centipoise.

COMPARATIVE EXAMPLE 3.

Upon putting 100g of alkylbenzene sulfonic acid prepared in the same way as in Example 5 in a 300 ml conical flask equipped with a condenser, by adding 18.5g of carbon tetrachloride and 1g of 30% hydrogen peroxide solution thereto with stirring, bleaching was effected at 50° C for 30 minutes, by the way, the viscosity of mixture in the early stage of bleaching was 70 centi-poise. The thus bleached sulfonic acid was neutralized with 4% aqueous solution of NaOH, then, a part of sulfonate was adjusted to be a 5% aqueous solution and measured about color thereof, the value was 95.

What is claimed is:

1. A method for bleaching sulfofatty acid material selected from the group consisting of sulfofatty acids having from 6 to 20 carbon atoms and esters thereof, which consists essentially of the steps of: mixing with said sulfofatty acid material from 0.5 to 20 percent by weight of a primary or secondary aliphatic alcohol having one to 12 carbon atoms, from 0.5 to 10 percent by weight of a peroxide bleaching agent, and from 0.1 to 10 percent by weight of water, all percentages being based on the weight of said sulfofatty acid material, and maintaining the mixture at 40° to 90° C for a period of time effective to bleach said sulfofatty acid material.

2. A method according to claim 1 in which said sulfofatty acid material is an ester of said sulfofatty acid and in which the product obtained by neutralizing the bleached sulfofatty acid material is substantially free of free sulfofatty acid.

3. A method according to claim 2 in which said ester is the sulfonated methyl ester of hydrogenated beef-tallow fatty acid.

4. A method according to claim 1 in which said sulfofatty acid material is prepared by sulfonating the corresponding fatty acid with SO₃ gas.

5. A method according to claim 4 in which said alcohol is selected from the group consisting of methyl alcohol, ethyl alcohol, propyl alcohol, hexyl alcohol, octyl alcohol, lauryl alcohol, isopropyl alcohol, ethylene glycol, glycerin and trimethylol propane.

6. A method according to claim 5 in which the amount of said alcohol is one to 15 percent by weight, the amount of said bleaching agent is one to 5 percent by weight, and the amount of water is one to 4 percent by weight, all percentages being based on the weight of said sulfofatty acid material.

7. A method according to claim 1, wherein said bleaching agent is selected from the group consisting of hydrogen peroxide, sodium perborate and sodium percarbonate.

8. A method according to claim 1, wherein the bleaching time is in the range of 15–120 minutes.

* * * * *